United States Patent [19]
Schweich, Jr. et al.

[11] Patent Number: 6,059,715
[45] Date of Patent: *May 9, 2000

[54] HEART WALL TENSION REDUCTION APPARATUS

[75] Inventors: Cyril J. Schweich, Jr., St. Paul; Todd J. Mortier, Minneapolis, both of Minn.

[73] Assignee: Myocor, Inc., St. Paul, Minn.

[*] Notice: This patent is subject to a terminal disclaimer.

[21] Appl. No.: 09/224,348

[22] Filed: Jan. 4, 1999

Related U.S. Application Data

[62] Division of application No. 08/778,277, Jan. 2, 1997.

[51] Int. Cl.⁷ .................................................. A61B 17/12
[52] U.S. Cl. .............................. 600/16; 600/37; 128/898
[58] Field of Search .................... 600/16–18, 37; 601/11; 623/3, 11; 128/897, 898

[56] References Cited

U.S. PATENT DOCUMENTS

| | | | |
|---|---|---|---|
| Re. 34,021 | 8/1992 | Mueller et al. | 604/51 |
| 4,192,293 | 3/1980 | Asrican | 600/18 |
| 4,261,342 | 4/1981 | Aranguren Duo | 128/1 |
| 4,372,293 | 2/1983 | Rosales et al. | 128/1 |
| 4,409,974 | 10/1983 | Freedland | 128/92 |
| 4,536,893 | 8/1985 | Parravicini | 623/3 |
| 4,936,857 | 1/1990 | Kulik | 623/3 |
| 4,944,753 | 7/1990 | Burgess et al. | 623/16 |
| 4,960,424 | 10/1990 | Grooters | 623/2 |
| 4,997,431 | 3/1991 | Isner et al. | 606/15 |
| 5,106,386 | 4/1992 | Isner et al. | 606/15 |
| 5,131,905 | 7/1992 | Grooters | 600/16 |
| 5,169,381 | 12/1992 | Snyders | 600/16 |
| 5,192,314 | 3/1993 | Daskalakis | 623/3 |
| 5,250,049 | 10/1993 | Michael | 606/72 |
| 5,284,488 | 2/1994 | Sideris | 606/213 |
| 5,385,528 | 1/1995 | Wilk | 600/18 |
| 5,433,727 | 7/1995 | Sideris | 606/213 |
| 5,450,860 | 10/1995 | O'Connor | 128/898 |
| 5,452,733 | 9/1995 | Sterman et al. | 128/898 |
| 5,458,574 | 10/1995 | Machold et al. | 604/101 |
| 5,496,305 | 3/1996 | Kittrell et al. | 606/15 |
| 5,509,428 | 4/1996 | Dunlop | 128/898 |
| 5,533,958 | 7/1996 | Wilk | 600/18 |
| 5,571,215 | 11/1996 | Sterman et al. | 623/66 |
| 5,584,803 | 12/1996 | Stevens et al. | 604/4 |
| 5,593,424 | 1/1997 | Northrup, III | 606/232 |
| 5,682,906 | 11/1997 | Sterman et al. | 128/898 |
| 5,702,343 | 12/1997 | Alferness | 607/37 |
| 5,718,725 | 2/1998 | Sterman et al. | 623/2 |
| 5,800,334 | 9/1998 | Wilk | 600/18 |
| 5,800,528 | 9/1998 | Lederman et al. | 623/3 |
| 5,814,097 | 9/1998 | Sterman et al. | 623/2 |
| 5,849,005 | 12/1998 | Garrison et al. | 606/1 |
| 5,855,614 | 1/1999 | Stevens et al. | 623/11 |
| 5,865,791 | 2/1999 | Whayne et al. | 604/49 |
| 5,957,977 | 9/1999 | Melvin | 623/3 |
| 5,984,857 | 11/1999 | Buck et al. | 600/16 |

FOREIGN PATENT DOCUMENTS

| | | |
|---|---|---|
| 0 583 012 | 2/1994 | European Pat. Off. . |
| 36 14 292 | 11/1987 | Germany . |
| 42 34 127 | 5/1994 | Germany . |
| 91/19465 | 12/1991 | WIPO . |
| 95/06447 | 3/1995 | WIPO . |
| 95/16476 | 6/1995 | WIPO . |
| 96/04852 | 2/1996 | WIPO . |

(List continued on next page.)

OTHER PUBLICATIONS

Carpentier et al., "Myocardial Substitution with a Stimulated Skeletal Muscle: First Successful Clinical Case," Letter to the Editor, p. 1267, Sep. 25, 1996.

(List continued on next page.)

*Primary Examiner*—Jeffrey R. Jastrzab
*Attorney, Agent, or Firm*—Finnegan, Henderson, Farabow, Garrett & Dunner, LLP

[57] ABSTRACT

An apparatus for treatment of a failing heart by reducing the wall tension therein. In one embodiment, the apparatus includes a tension member for drawing at least two walls of a heart chamber toward each other.

183 Claims, 3 Drawing Sheets

FOREIGN PATENT DOCUMENTS

| | | |
|---|---|---|
| 96/40356 | 12/1996 | WIPO . |
| 97/24101 | 7/1997 | WIPO . |
| 98/03213 | 1/1998 | WIPO . |
| 98/18393 | 5/1998 | WIPO . |
| 98/26738 | 6/1998 | WIPO . |
| 98/32382 | 7/1998 | WIPO . |
| 99/13777 | 3/1999 | WIPO . |
| 99/44534 | 9/1999 | WIPO . |

OTHER PUBLICATIONS

Ianuzzo et al., "Preservation of the Latissimus Dorsi Muscle During Cardiomyoplasty Surgery," *J. Card. Surg.*, 1996:11:99–108.

Ianuzzo et al., "On Preconditioning of Skeletal Muscle: Application to Dynamic Cardiomyoplasty," Invited Commentary, *J. Card. Surg.*, 1996:11:109–110.

Chachques et al., "Latissimus Dorsi Dynamic Cardiomyoplasty," *Ann. Thorac. Surg.*, 1989:47:600–604.

Moreira et al., "Latissimus Dorsi Cardiomyoplasty in the Treatment of Patients with Dilated Cardiomyopathy," Supplement IV Circulation, Sep. 25, 1996, 7 pages.

Lucas et al., "Long–Term Follow–Up (12 to 35 Weeks) After Dynamic Cardiomyoplasty," *JACC*, vol. 22, No. 3, Sep. 1993:758–67.

Batista et al., "Partial Left Ventriculectomy to Improve Left Ventricular Function in End–Stage Heart Disease," *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally III Cardiac Transplant Candidates," *Ann. Thorac. Surg.*, 1990:49:261–71.

Wampler et al., "Treatment of Cardiogenic Shock with the Hemopump Left Ventricular Assist Device," *Ann. Thorac. Surg.*, 1991:52:506–13.

McCarthy et al., "Clinical Experience with the Novacor Ventricular Assist System," *J. Thorac. Cardiovasc. Surg.*, 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632–636.

Bearnson et al., "Development of a Prototype Magnetically Suspended Rotor Ventricular Assist Device," *ASAIO Journal*, 1996, pp. 275–280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372–375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED" Wins NIH Grant to Develop Calcification–Resistant Plastic Heart Valve, 1 page.

Press Release dated Aug. 25, 1995, "ABIOMED Wins Research Grant from NIH to Develop Suturing Instrument for Abdominal Surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS–5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device–Blood Compatibility," *ASAIO Journal*, 1994, pp. 619–624.

Farrar et al., "A New Skeletal Muscle Linear–Pull Energy Convertor as a Power Source for Prosthetic Support Devices," *The Journal of Heart & Lung Transplantation*, vol. 11, No. 5, Sep., 1992, pp. 341–349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End–Stage Cardiomyopathy," *American Heart Journal*, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in Mitral Regurgitation," *Br. Heart J.*, vol. 49, 1983, pp. 328–333.

Pitarys II et al., "Long–Term Effects of Excision of the Mitral Apparatus on Global and Regional Ventricular Function in Humans," *JACC*, vol. 15, No. 3, Mar. 1, 1990, pp. 557–563.

Bolling et al., "Surgery for Acquired Heart Disease/Early Outcome of Mitral Valve Reconstruction in Patients with End–Stage Cardiomyopathy," *The Journal of Thoracic and Cardiovascular Surgery*, vol. 109, No. 4, Apr. 1995, pp. 676–683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138–1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation Presented at the 77th Annual Meeting of the American Association of Thoracic Surgeons, May 1997, 33 pages.

Alonso–Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404–406, Oct. 1987.

Boyd et al., "Tricuspid Annuloplasty," *The Journal of Thoracic Cardiovascular Surgery*, vol. 68, No. 3, Sep. 1974, 8 pages.

Edie, M.D. et al., "Surgical repair of single ventricle," *The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

Lev, M.D., et al., "Single (Primitive) Ventricle," *Circulation*, vol. 39, May, 1969, pp. 577–591.

Westaby with Bosher, "Landmarks in Cardiac Surgery," 1997, pp. 198–199.

Shumacker, "Cardiac Aneurysms," *The Evolution of Cardiac Surgery*, 1992, pp. 159–165.

Feldt, M.D., "Current status of the septation procedure for univentricular heart," *The Journal of Thoracic and Cardiovascular Surgery*, vol. 82, No. 1, Jul., 1981, pp. 93–97.

Doty, M.D., "Septation of the univentricular heart," *The Journal of Thoracic and Cardiovascular Surgery*, vol. 78, No. 3, Sep., 1979, pp. 423–430.

Savage, M.D., "Repair of left ventricular aneurysm," *The Journal of Thoracic and Cardiovascular Surgery*, vol. 104, No. 3, Sep., 1992, pp. 752–762.

Cox, "Left Ventricular Aneurysms: Pathophysiologic Observations and Standard Resection," *Seminars in Thoracic and Cardiovascular Surgery*, vol. 9, No. 2, Apr., 1997, pp. 113–122.

Melvin, "Ventricular Radius Reduction Without Resection: A Computational Analysis," *ASAIO Journal*, 45:160–165, 1999.

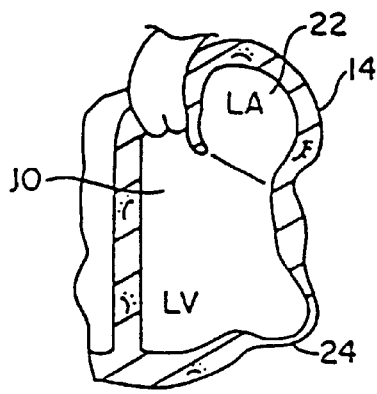
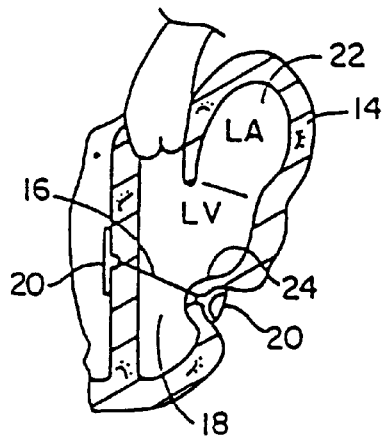
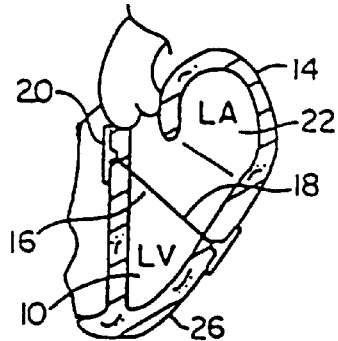
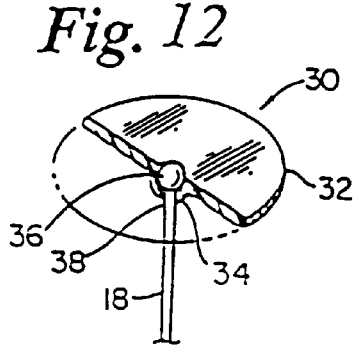
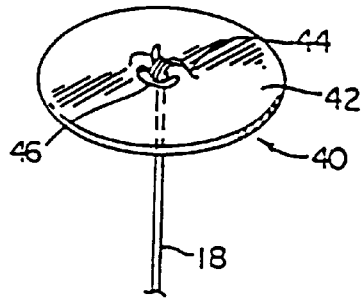
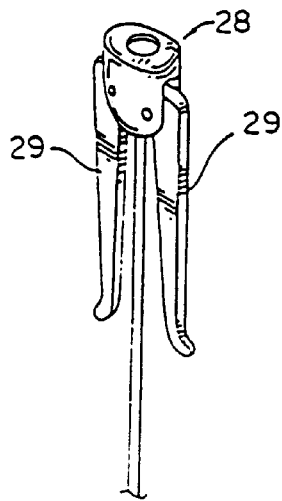
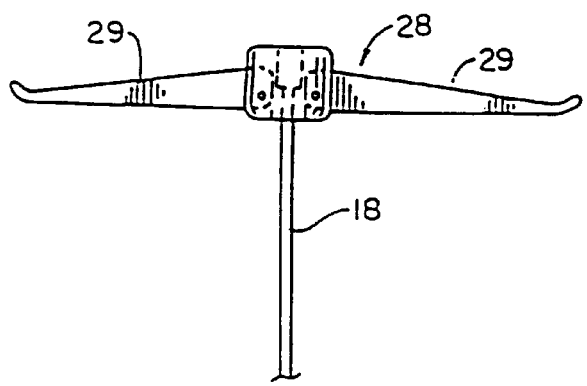

HEART WALL TENSION REDUCTION APPARATUS

This application is a division of Ser. No. 08/778,277 filed Jan. 2, 1997.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes like digoxin are cardiac glycosides and function to increase cardiac output by increasing the force and speed of cardiac muscle contraction. These drug therapies offer some beneficial effects but do not stop the progression of the disease.

Assist devices include mechanical pumps and electrical stimulators. Mechanical pumps reduce the load on the heart by performing all or part of the pumping function normally done by the heart. Currently, mechanical pumps are used to sustain the patient while a donor heart for transplantation becomes available for the patient. Electrical stimulation such as biventricular pacing have been investigated for the treatment of patients with dilated cardiomyopathy.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a non-pharmacological, passive apparatus for the treatment of a failing heart. The device is configured to reduce the tension in the heart wall. It is believed to reverse, stop or slow the disease process of a failing heart as it reduces the energy consumption of the failing heart, decrease in isovolumetric contraction, increases sarcomere shortening during contraction and an increase in isotonic shortening in turn increases stroke volume. The device reduces wall tension during diastole (preload) and systole.

In one embodiment, the apparatus includes a tension member for drawing at least two walls of the heart chamber toward each other to reduce the radius or area of the heart chamber in at least one cross sectional plane. The tension member has anchoring member disposed at opposite ends for engagement with the heart or chamber wall.

In another embodiment, the apparatus includes a compression member for drawing at least two walls of a heart chamber toward each other. In one embodiment, the compression member includes a balloon. In another embodiment of the apparatus, a frame is provided for supporting the compression member.

Yet another embodiment of the invention includes a clamp having two ends biased toward one another for drawing at least two walls of a heart chamber toward each other. The clamp includes at least two ends having atraumatic anchoring member disposed thereon for engagement with the heart or chamber wall.

BRIEF DESCRIPTION OF THE DRAWINGS

FIG. 7 is a vertical cross-section of the left ventricle and atrium, the left ventricle having scar tissue;

FIG. 8 is a vertical cross-section of the heart of FIG. 7 showing the splint of FIG. 1 drawing the scar tissue toward the opposite wall of the left ventricle;

FIG. 9 is a vertical cross-section of the left ventricle and atrium of a human heart showing a version of the splint of FIG. 1 having an elongate anchor bar;

FIG. 10 is a side view of an undeployed hinged anchor member;

FIG. 11 is a side view of a deployed hinged anchor member of FIG. 10;

FIG. 12 is a cross-sectional view of an captured ball anchor member;

FIG. 13 is a perspective view of a cross bar anchor member;

DETAILED DESCRIPTION OF THE INVENTION

Figure 1:
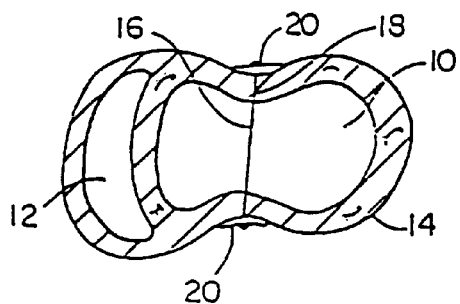
FIG. 1 is a transverse cross-section of the left and right ventricles of a human heart showing the placement of a splint in accordance with the present invention.

Referring now to the drawings wherein like reference numerals refer to like elements throughout the several views, FIG. 1 shows a transverse cross-section of a left ventricle 10 and a right ventricle 12 of a human heart 14. Extending through the left ventricle is a splint 16 including a tension member 18 and oppositely disposed anchors 20. Splint 16 as shown in FIG. 1 has been positioned to draw opposite walls of left ventricle 10 toward each other to reduce the "radius" of the left ventricular cross-section or the cross-sectional area thereof to reduce left ventricular wall stresses. It should be understood that although the splint 16 and the alternative devices disclosed herein are described in relation to the left ventricle of a human heart, these devices could also be used to reduce the radius or cross-sectional area of the other chambers of a human heart in transverse or vertical directions, or at an angle between the transverse and vertical.

Figure 2:
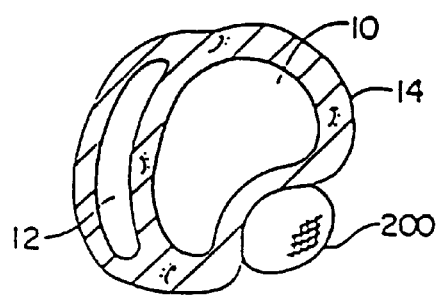
FIG. 2 is a transverse cross-section of the left and right ventricles of a human heart showing the placement of a balloon device in accordance with the present invention.

FIG. 2 discloses an alternate embodiment of the present invention, wherein a balloon 200 is deployed adjacent the left ventricle. The size and degree of inflation of the balloon can be varied to reduce the radius or cross-sectional area of left ventricle 10 of heart 14.

Figure 3:
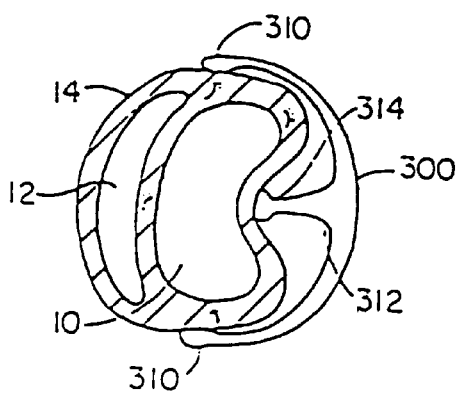
FIG. 3 is a transverse cross-section of the left and right ventricles of a human heart showing the placement of an external compression frame structure in accordance with the present invention.

FIG. 3 shows yet another alternative embodiment of the present invention deployed with respect to left ventricle 10 of human heart 14. Here a compression frame structure 300 is engaged with heart 14 at atraumatic anchor pads 310. A compression member 312 having an atraumatic surface 314 presses against a wall of left ventricle 10 to reduce the radius or cross-sectional area thereof.

Figure 4:
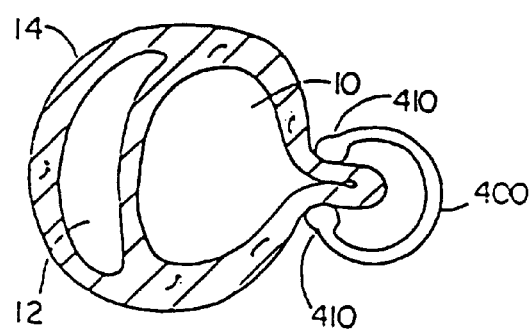
FIG. 4 is a transverse cross-section of the left and right ventricles of a human heart showing a clamp in accordance with the present invention.

FIG. 4 is a transverse cross-sectional view of human heart 14 showing yet another embodiment of the present invention. In this case a clamp 400 having atraumatic anchor pads 410 biased toward each other is shown disposed on a wall of left ventricle 10. Here the radius or cross-sectional area of left ventricle 10 is reduced by clamping off the portion of the wall between pads 410. Pads 410 can be biased toward each other and/or can be held together by a locking device.

Each of the various embodiments of the present invention disclosed in FIGS. 1–4 can be made from materials which can remain implanted in the human body indefinitely. Such biocompatible materials are well-known to those skilled in the art of clinical medical devices.

Figure 5:
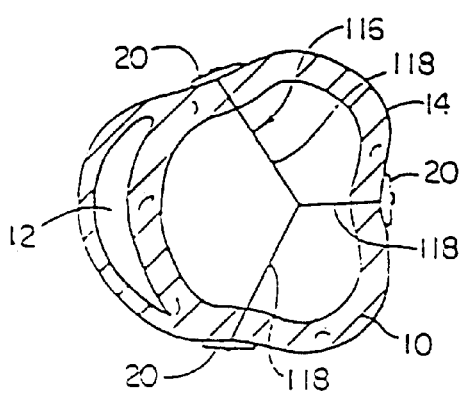
FIG. 5 is a transverse cross-section of the left and right ventricles of a human heart showing a three tension member version of the splint of FIG. 1.
Figure 6:
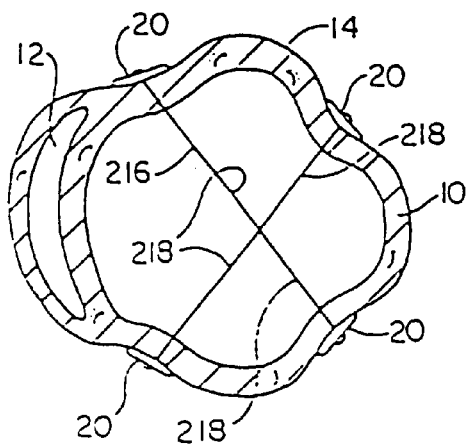
FIG. 6 is a transverse cross-section of the left and right ventricles of a human heart showing a four tension member version of the splint shown in FIG. 1.

FIG. 5 shows an alternate embodiment of the splint of FIG. 1 referred to in FIG. 5 by the numeral 116. The embodiment 116 shown in FIG. 5 includes three tension members 118 as opposed to a single tension member 18 as shown in FIG. 1. FIG. 6 shows yet another embodiment of the splint 216 having four tension members 218. It is anticipated that in some patients, the disease process of the failing heart may be so advanced that three, four or more tension members may be desirable to reduce the heart wall stresses more substantially than possible with a single tension member as shown in FIG. 1.

FIG. 7 is a partial vertical cross-section of human heart 14 showing left ventricle 10 and left atrium 22. As shown in FIG. 7, heart 14 includes a region of scar tissue 24 associated with an aneurysm or ischemia. As shown in FIG. 7, the scar tissue 24 increases the radius or cross-sectional area of left ventricle 10 in the region affected by the scar tissue. Such an increase in the radius or cross-sectional area of the left ventricle will result in greater wall stresses on the walls of the left ventricle.

FIG. 8 is a vertical cross-sectional view of the heart 14 as shown in FIG. 7, wherein a splint 16 has been placed to draw the scar tissue 24 toward an opposite wall of left ventricle 10. As a consequence of placing splint 16, the radius or cross-sectional area of the left ventricle affected by the scar tissue 24 is reduced. The reduction of this radius or cross-sectional area results in reduction in the wall stress in the left ventricular wall and thus improves heart pumping efficiency.

FIG. 9 is a vertical cross-sectional view of left ventricle 10 and left atrium 22 of heart 14 in which a splint 16 has been placed. As shown in FIG. 9, splint 16 includes an alternative anchor 26. The anchor 26 is preferably an elongate member having a length as shown in FIG. 9 substantially greater than its width (not shown). Anchor bar 26 might be used to reduce the radius or cross-sectional area of the left ventricle in an instance where there is generalized enlargement of left ventricle 10 such as in idiopathic dilated cardiomyopathy. In such an instance, bar anchor 26 can distribute forces more widely than anchor 20.

FIGS. 10 and 11 are side views of a hinged anchor 28 which could be substituted for anchors 20 in undeployed and deployed positions respectively. Anchor 28 as shown in FIG. 10 includes two legs similar to bar anchor 26. Hinged anchor 28 could include additional legs and the length of those legs could be varied to distribute the force over the surface of the heart wall. In addition there could be webbing between each of the legs to give anchor 28 an umbrella-like appearance. Preferably the webbing would be disposed on the surface of the legs which would be in contact with the heart wall.

FIG. 12 is a cross-sectional view of a capture ball anchor 30. Capture ball anchor 30 can be used in place of anchor 20. Capture ball anchor 30 includes a disk portion 32 to distribute the force of the anchor on the heart wall, and a recess 34 for receiving a ball 36 affixed to an end of tension member 18. Disk 32 and recess 34 include a side groove which allows tension member 38 to be passed from an outside edge of disk 32 into recess 34. Ball 36 can then be advanced into recess 34 by drawing tension member 18 through an opening 38 in recess 34 opposite disk 32.

FIG. 13 is a perspective view of a cross bar anchor 40. The cross bar anchor 40 can be used in place of anchors 20. The anchor 40 preferably includes a disk or pad portion 42 having a cross bar 44 extending over an opening 46 in pad 42. Tension member 18 can be extended through opening 46 and tied to cross bar 42 as shown.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart. In the case of the splint 16 shown in FIG. 1, a canula can be used to pierce both walls of the heart and one end of the splint can be advanced through the canula from one side of the heart to the opposite side where an anchor can be affixed or deployed. Likewise, an anchor is affixed or deployed at the opposite end of splint 16.

Figure 14:
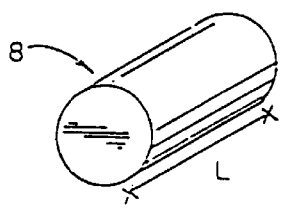
FIG. 14 is a idealized cylindrical model of a left ventricle of a human heart.

FIG. 14 is a view of a cylinder or idealized heart chamber 48 which is used to illustrate the reduction of wall stress in a heart chamber as a result of deployment of the splint in accordance with the present invention. The model used herein and the calculations related to this model are intended merely to illustrate the mechanism by which wall stress is reduced in the heart chamber. No effort is made herein to quantify the actual reduction which would be realized in any particular in vivo application.

Figure 15:
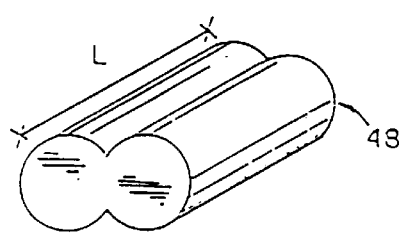
FIG. 15 is a splinted model of the left ventricle of FIG. 14.

FIG. 15 is a view of the idealized heart chamber 48 of FIG. 14 wherein the chamber has been splinted along its length L such that a "figure eight" cross-section has been formed along the length thereof. It should be noted that the perimeter of the circular transverse cross-section of the chamber in FIG. 14 is equal to the perimeter of the figure eight transverse cross-section of FIG. 15. For purposes of this model, opposite lobes of the figure in cross-section are assumed to be mirror images.

Figure 16:
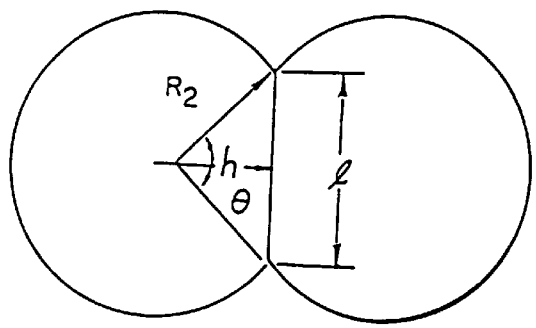
FIG. 16 is a transverse cross-sectional view of FIG. 15 showing various modeling parameters.

FIG. 16 shows various parameters of the FIG. 8 cross-section of the splinted idealized heart chamber of FIG. 15. Where l is the length of the splint between opposite walls of the chamber, $R_2$ is the radius of each lobe, θ is the angle between the two radii of one lobe which extends to opposite ends of the portion of the splint within chamber 48 and h is the height of the triangle formed by the two radii and the portion of the splint within the chamber 48 ($R_1$ is the radius of the cylinder of FIG. 14). These various parameters are related as follows:

$$h = R_2 \cos(\theta/2)$$

$$l = 2R_2 \sin(\theta/2)$$

$$R_2 = R_1 \pi / (2\pi - \theta)$$

From these relationships, the area of the figure eight cross-section can be calculated by:

$$A_2 = 2\pi (R_2)^2 (1 - \theta/2\pi) + hl$$

Where chamber 48 is unsplinted as shown in FIG. 14 $A_1$, the original cross-sectional area of the cylinder is equal to $A_2$ where θ=180°, h=0 and l=2$R_2$. Volume equals $A_2$ times length L and circumferential wall tension equals pressure within the chamber times $R_2$ times the length L of the chamber.

Thus, for example, with an original cylindrical radius of four centimeters and a pressure within the chamber of 140 mm of mercury, the wall tension T in the walls of the cylinder is 104.4 newtons. When a 3.84 cm splint is placed as shown in FIGS. 15 and 16 such that l=3.84 cm, the wall tension T is 77.33 newtons.

Figure 17:
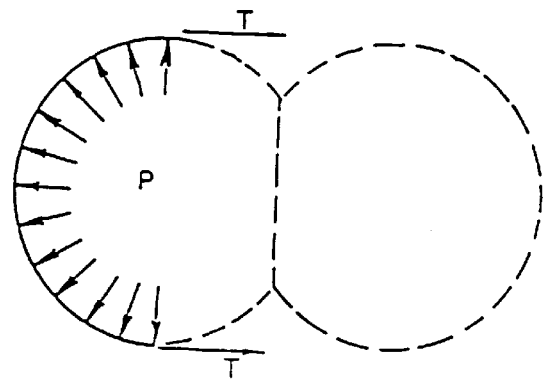
FIG. 17 is a transverse cross-section of the splinted left ventricle of FIG. 15 showing a hypothetical force distribution.
Figure 18:
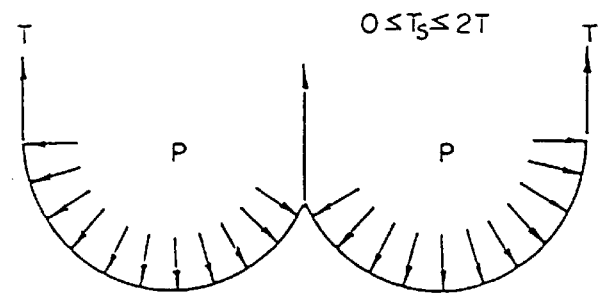
FIG. 18 is a second transverse cross-sectional view of the model left ventricle of FIG. 15 showing a hypothetical force distribution.

FIGS. 17 and 18 show a hypothetical distribution of wall tension T and pressure P for the figure eight cross-section. As θ goes from 180° to 0°, tension $T_0$ in the splint goes from 0 to a 2T load where the chamber walls carry a T load.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A method for treating a heart, the method comprising the steps of:

placing a member in a position adjacent a wall of a heart chamber so that the member draws portions of the chamber wall towards each other; and fixing the member in the position so that the portions of the chamber wall remain in a non-contacting relationship.

2. The method of claim 1, wherein the placing step includes placing the member within the chamber.

3. The method of claim 2, wherein the member includes a tension member.

4. The method of claim 3, wherein the fixing step includes attaching a first anchor to a first end of the tension member and attaching a second anchor to a second end of the tension member.

5. The method of claim 4, wherein the fixing step includes engaging walls of the chamber external to the chamber with the first and second anchors.

6. The method of claim 2, wherein the member includes a plurality of tension members.

7. The method of claim 1, wherein the placing step includes placing the member external the chamber.

8. The method of claim 7, wherein the member includes a compression member.

9. The method of claim 7, wherein the member includes a clamp.

10. The method of claim 1, wherein the placing step includes placing the member transverse the chamber.

11. The method of claim 1, wherein the placing step includes placing the member in the position so that the member draws scar tissue of the chamber wall towards an opposite portion of the chamber wall.

12. A method for treating a heart, the method comprising the steps of:
 placing a member in a position adjacent a wall of an intact heart chamber so that the member draws portions of the chamber wall towards each other; and
 fixing the member in the position so that all interior parts of the chamber remain in direct fluid communication.

13. The method of claim 12, wherein the placing step includes placing the member within the chamber.

14. The method of claim 13, wherein the member includes a tension member.

15. The method of claim 14, wherein the fixing step includes attaching a first anchor to a first end of the tension member and attaching a second anchor to a second end of the tension member.

16. The method of claim 15, wherein the fixing step includes engaging walls of the chamber external to the chamber with the first and second anchors.

17. The method of claim 13, wherein the member includes a plurality of tension members.

18. The method of claim 12, wherein the placing step includes placing the member external the chamber.

19. The method of claim 18, wherein the member includes a compression member.

20. The method of claim 18, wherein the member includes a clamp.

21. The method of claim 12, wherein the placing step includes placing the member transverse the chamber.

22. The method of claim 12, wherein the placing step includes placing the member in the position so that the member draws scar tissue of the chamber wall towards an opposite portion of the chamber wall.

23. A method for treating a heart, the method comprising the steps of:
 placing a member in a position adjacent a wall of an intact heart chamber so that the member alters a shape of the chamber during systole; and
 fixing the member in the position so that all interior parts of the chamber remain in direct fluid communication.

24. The method of claim 23, wherein the placing step includes placing the member within the chamber.

25. The method of claim 24, wherein the member includes a tension member.

26. The method of claim 25, wherein the fixing step includes attaching a first anchor to a first end of the tension member and attaching a second anchor to a second end of the tension member.

27. The method of claim 26, wherein the fixing step includes engaging walls of the chamber external to the chamber with the first and second anchors.

28. The method of claim 24, wherein the member includes a plurality of tension members.

29. The method of claim 23, wherein the placing step includes placing the member external the chamber.

30. The method of claim 29, wherein the member includes a compression member.

31. The method of claim 29, wherein the member includes a clamp.

32. The method of claim 23, wherein the placing step includes placing the member transverse the chamber.

33. The method of claim 23, wherein the placing step includes placing the member in the position so that the member draws scar tissue of the chamber wall towards an opposite portion of the chamber wall.

34. The method of claim 23, wherein the member alters the shape of the chamber during isotonic contraction.

35. The method of claim 23, wherein the member alters the shape of the chamber during isovolumetric contraction.

36. The method of claim 23, wherein the member alters the shape of the chamber during a complete cardiac cycle.

37. The method of claim 23, wherein the member alters the shape of the chamber during diastole.

38. A method for treating a heart, the method comprising the steps of:
 placing a member in a position adjacent a wall of an intact heart chamber so that the member reduces a radius of the chamber during systole; and
 fixing the member in the position so that all interior parts of the chamber remain in direct fluid communication.

39. The method of claim 38, wherein the placing step includes placing the member within the chamber.

40. The method of claim 39, wherein the member includes a tension member.

41. The method of claim 40, wherein the fixing step includes attaching a first anchor to a first end of the tension member and attaching a second anchor to a second end of the tension member.

42. The method of claim 41, wherein the fixing step includes engaging walls of the chamber external to the chamber with the first and second anchors.

43. The method of claim 39, wherein the member includes a plurality of tension members.

44. The method of claim 38, wherein the placing step includes placing the member external the chamber.

45. The method of claim 44, wherein the member includes a compression member.

46. The method of claim 44, wherein the member includes a clamp.

47. The method of claim 38, wherein the placing step includes placing the member transverse the chamber.

48. The method of claim 38, wherein the placing step includes placing the member in the position so that the member draws scar tissue of the chamber wall towards an opposite portion of the chamber wall.

49. The method of claim 38, wherein the member reduces the radius of the chamber during isotonic contraction.

50. The method of claim 38, wherein the member reduces the radius of the chamber during isovolumetric contraction.

51. The method of claim 38, wherein the member reduces the radius of the chamber during a complete cardiac cycle.

52. The method of claim 38, wherein the member reduces the radius of the chamber during diastole.

53. A method for treating a heart, the method comprising the steps of:
 placing a member in a position adjacent a wall of an intact heart chamber so that the member reduces a cross-sectional area of the chamber during systole; and
 fixing the member in the position so that all interior parts of the chamber remain in direct fluid communication.

54. The method of claim 53, wherein the placing step includes placing the member within the chamber.

55. The method of claim 54, wherein the member includes a tension member.

56. The method of claim 55, wherein the fixing step includes attaching a first anchor to a first end of the tension member and attaching a second anchor to a second end of the tension member.

57. The method of claim 56, wherein the fixing step includes engaging walls of the chamber external to the chamber with the first and second anchors.

58. The method of claim 54, wherein the member includes a plurality of tension members.

59. The method of claim 53, wherein the placing step includes placing the member external the chamber.

60. The method of claim 59, wherein the member includes a compression member.

61. The method of claim 59, wherein the member includes a clamp.

62. The method of claim 59, wherein the placing step includes placing the member transverse the chamber.

63. The method of claim 59, wherein the placing step includes placing the member in the position so that the member draws scar tissue of the chamber wall towards an opposite portion of the chamber wall.

64. The method of claim 53, wherein the member reduces the cross-sectional area of the chamber during isotonic contraction.

65. The method of claim 53, wherein the member reduces the cross-sectional area of the chamber during isovolumetric contraction.

66. The method of claim 53, wherein the member reduces the cross-sectional area of the chamber during a complete cardiac cycle.

67. The method of claim 53, wherein the member reduces the cross-sectional area of the chamber during diastole.

68. A method for treating a heart, the method comprising the steps of:
placing a member in a position adjacent portions of a wall of a heart chamber so that the member alters a shape of the chamber during systole; and
fixing the member in the position so that the portions of the chamber wall remain in a non-contacting relationship.

69. The method of claim 68, wherein the placing step includes placing the member within the chamber.

70. The method of claim 69, wherein the member includes a tension member.

71. The method of claim 70, wherein the fixing step includes attaching a first anchor to a first end of the tension member and attaching a second anchor to a second end of the tension member.

72. The method of claim 71, wherein the fixing step includes engaging walls of the chamber external to the chamber with the first and second anchors.

73. The method of claim 69, wherein the member includes a plurality of tension members.

74. The method of claim 68, wherein the placing step includes placing the member external the chamber.

75. The method of claim 74, wherein the member includes a compression member.

76. The method of claim 74, wherein the member includes a clamp.

77. The method of claim 68, wherein the placing step includes placing the member transverse the chamber.

78. The method of claim 68, wherein the placing step includes placing the member in the position so that the member draws scar tissue of the chamber wall towards an opposite portion of the chamber wall.

79. The method of claim 68, wherein the member alters the shape of the chamber during isotonic contraction.

80. The method of claim 68, wherein the member alters the shape of the chamber during isovolumetric contraction.

81. The method of claim 68, wherein the member alters the shape of the chamber during a complete cardiac cycle.

82. The method of claim 68, wherein the member alters the shape of the chamber during diastole.

83. A method for treating a heart, the method comprising the steps of:
placing a member in a position adjacent portions of a wall of a heart chamber so that the member reduces a radius of the chamber during systole; and
fixing the member in the position so that the portions of the chamber wall remain in a non-contacting relationship.

84. The method of claim 83, wherein the placing step includes placing the member within the chamber.

85. The method of claim 84, wherein the member includes a tension member.

86. The method of claim 85, wherein the fixing step includes attaching a first anchor to a first end of the tension member and attaching a second anchor to a second end of the tension member.

87. The method of claim 86, wherein the fixing step includes engaging walls of the chamber external to the chamber with the first and second anchors.

88. The method of claim 84, wherein the member includes a plurality of tension members.

89. The method of claim 83, wherein the placing step includes placing the member external the chamber.

90. The method of claim 89, wherein the member includes a compression member.

91. The method of claim 89, wherein the member includes a clamp.

92. The method of claim 83, wherein the placing step includes placing the member transverse the chamber.

93. The method of claim 83, wherein the placing step includes placing the member in the position so that the member draws scar tissue of the chamber wall towards an opposite portion of the chamber wall.

94. The method of claim 83, wherein the member reduces the radius of the chamber during isotonic contraction.

95. The method of claim 83, wherein the member reduces the radius of the chamber during isovolumetric contraction.

96. The method of claim 83, wherein the member reduces the radius of the chamber during a complete cardiac cycle.

97. The method of claim 83, wherein the member reduces the radius of the chamber during diastole.

98. A method for treating a heart, the method comprising the steps of:
placing a member in a position adjacent portions of a wall of a heart chamber so that the member reduces a cross-sectional area of the chamber during systole; and
fixing the member in the position so that the portions of the chamber wall remain in a non-contacting relationship.

99. The method of claim 98, wherein the placing step includes placing the member within the chamber.

100. The method of claim 99, wherein the member includes a tension member.

101. The method of claim 100, wherein the fixing step includes attaching a first anchor to a first end of the tension member and attaching a second anchor to a second end of the tension member.

102. The method of claim 101, wherein the fixing step includes engaging walls of the chamber external to the chamber with the first and second anchors.

103. The method of claim 99, wherein the member includes a plurality of tension members.

104. The method of claim 98, wherein the placing step includes placing the member external the chamber.

105. The method of claim 104, wherein the member includes a compression member.

106. The method of claim 104, wherein the member includes a clamp.

107. The method of claim 98, wherein the placing step includes placing the member transverse the chamber.

108. The method of claim 98, wherein the placing step includes placing the member in the position so that the member draws scar tissue of the chamber wall towards an opposite portion of the chamber wall.

109. The method of claim 98, wherein the member reduces the cross-sectional area of the chamber during isotonic contraction.

110. The method of claim 98, wherein the member reduces the cross-sectional area of the chamber during isovolumetric contraction.

111. The method of claim 98, wherein the member reduces the cross-sectional area of the chamber during a complete cardiac cycle.

112. The method of claim 98, wherein the member reduces the cross-sectional area of the chamber during diastole.

113. A method for treating a heart, the method comprising the steps of:
   applying a force at a point on a wall of a heart chamber to change a shape of the chamber during systole; and
   controlling the force such that a space remains between the wall proximate the point on the wall and an opposing wall of the chamber.

114. The method of claim 113, wherein the force is applied and controlled by a member within the chamber having anchors external the chamber.

115. The method of claim 114, wherein the member includes a tension member transverse the chamber.

116. The method of claim 114, wherein the member includes a plurality of tension members each transverse the chamber.

117. The method of claim 113, wherein the force is applied and controlled by a member external the chamber having anchors external the chamber.

118. The method of claim 117, wherein the member includes a compression member.

119. The method of claim 117, wherein the member includes a clamp.

120. The method of claim 113, wherein the shape of the chamber is changed during isotonic contraction.

121. The method of claim 113, wherein the shape of the chamber is changed during isovolumetric contraction.

122. The method of claim 113, wherein the shape of the chamber is changed during a complete cardiac cycle.

123. The method of claim 113, wherein the shape of the chamber is changed during diastole.

124. An apparatus for treating a heart, comprising:
   a member adapted to remain external a heart chamber and contact a wall of the heart chamber external to the chamber during systole, the member including a first portion for contacting a first portion of the chamber wall external to the chamber and a second portion for contacting a second portion of the chamber wall external to the chamber, wherein the member is adapted to alter a shape of the chamber.

125. The apparatus of claim 124, wherein the member is adapted to alter the shape of the chamber so that internal portions of the chamber wall remain in a noncontacting relationship.

126. The apparatus of claim 124, wherein the member is adapted to alter the shape of the chamber so that all interior parts of the chamber remain in direct fluid communication.

127. The apparatus of claim 124, wherein the second portion of the chamber wall is opposite to the first portion of the chamber wall.

128. The apparatus of claim 124, wherein the first and second portions of the member are adapted to draw interior portions of the wall of the chamber towards each other.

129. The apparatus of claim 124, wherein the member is adapted to reduce a cross-sectional area of the chamber.

130. The apparatus of claim 124, wherein the member is adapted to alter the shape of the chamber during isotonic contraction.

131. The apparatus of claim 124, wherein the member is adapted to alter the shape of the chamber during isovolumetric contraction.

132. The apparatus of claim 124, wherein the member is adapted to alter the shape of the chamber during a complete cardiac cycle.

133. The apparatus of claim 124, wherein the member is adapted to alter the shape of the chamber during diastole.

134. An apparatus for treating a heart, comprising:
   a member adapted to remain external a heart chamber and contact a wall of the heart chamber external to the chamber, the member including a first portion for contacting a first portion of the chamber wall external to the chamber and a second portion for contacting a second portion of the chamber wall external to the chamber and opposite to the first portion of the chamber wall, wherein the first and second portions of the member are adapted to alter a shape of the chamber and draw interior portions of the chamber wall towards each other so that the interior portions of the chamber wall remain in a noncontacting relationship and all interior parts of the chamber remain in direct fluid communication.

135. A method for treating a heart, the method comprising the steps of:
   providing a member having a first portion and a second portion; and
   altering a shape of a heart chamber during systole by engaging a first portion of a wall of the chamber external to the chamber with the first portion of the member and engaging a second portion of the chamber wall external to the chamber with the second portion of the member.

136. The method of claim 135, wherein the second portion of the chamber wall is opposite to the first portion of the chamber wall.

137. The method of claim 135, wherein the altering step includes maintaining internal portions of the chamber wall in a noncontacting relationship.

138. The method of claim 135, wherein the altering step includes maintaining all interior parts of the chamber in direct fluid communication.

139. The method of claim 135, wherein the altering step includes reducing a cross-sectional area of the chamber.

140. The method of claim 135, wherein the altering step includes drawing interior portions of the chamber wall towards each other.

141. The method of claim 135, wherein the shape of the chamber is altered during isotonic contraction.

142. The method of claim 135, wherein the shape of the chamber is altered during isovolumetric contraction.

143. The method of claim 135, wherein the shape of the chamber is altered during a complete cardiac cycle.

144. The method of claim 135, wherein the shape of the chamber is altered during diastole.

145. A method for treating a heart, the method comprising the steps of:
   placing a member within an intact heart chamber so that the member alters a shape of the chamber; and
   fixing the member to the chamber so that all interior parts of the chamber remain in direct fluid communication.

146. The method of claim 145, wherein the member includes a tension member.

147. The method of claim 146, wherein the fixing step includes attaching a first anchor to a first end of the tension member and attaching a second anchor to a second end of the tension member.

148. The method of claim 147, wherein the fixing step includes engaging walls of the chamber external to the chamber with the first and second anchors.

149. The method of claim 145, wherein the placing step includes placing the member transverse the chamber.

150. The method of claim 145, wherein the placing step includes placing the member so that the member draws scar tissue of a chamber wall towards an opposite portion of the chamber wall.

151. A method for treating a heart, the method comprising the steps of:

placing a member within an intact heart chamber so that the member reduces a radius of the chamber; and fixing the member to the chamber so that all interior parts of the chamber remain in direct fluid communication.

152. The method of claim 151, wherein the member includes a tension member.

153. The method of claim 152, wherein the fixing step includes attaching a first anchor to a first end of the tension member and attaching a second anchor to a second end of the tension member.

154. The method of claim 153, wherein the fixing step includes engaging walls of the chamber external to the chamber with the first and second anchors.

155. The method of claim 151, wherein the placing step includes placing the member transverse the chamber.

156. The method of claim 151, wherein the placing step includes placing the member so that the member draws scar tissue of a chamber wall towards an opposite portion of the chamber wall.

157. A method for treating a heart, the method comprising the steps of:

placing a member within an intact heart chamber so that the member reduces a cross-sectional area of the chamber; and fixing the member to the chamber so that all interior parts of the chamber remain in direct fluid communication.

158. The method of claim 157, wherein the member includes a tension member.

159. The method of claim 158, wherein the fixing step includes attaching a first anchor to a first end of the tension member and attaching a second anchor to a second end of the tension member.

160. The method of claim 159, wherein the fixing step includes engaging walls of the chamber external to the chamber with the first and second anchors.

161. The method of claim 157, wherein the placing step includes placing the member transverse the chamber.

162. The method of claim 157, wherein the placing step includes placing the member so that the member draws scar tissue of a chamber wall towards an opposite portion of the chamber wall.

163. A method for treating a heart, the method comprising the steps of:

placing a member within a heart chamber at portions of a wall of the chamber so that the member alters a shape of the chamber; and fixing the member to the chamber so that the portions of the chamber wall remain in a non-contacting relationship.

164. The method of claim 163, wherein the member includes a tension member.

165. The method of claim 164, wherein the fixing step includes attaching a firstt anchor to a first end of the tension member and attaching a second anchor to a second end of the tension member.

166. The method of claim 165, wherein the fixing step includes engaging walls of the chamber external to the chamber with the first and second anchors.

167. The method of claim 163, wherein the placing step includes placing the member transverse the chamber.

168. The method of claim 163, wherein the placing step includes placing the member so that the member draws scar tissue of a chamber wall towards an opposite portion of the chamber wall.

169. A method for treating a heart, the method comprising the steps of:

placing a member within a heart chamber at portions of a wall of the chamber So that the member reduces a radius of the chamber; and fixing the member to the chamber so that the portions of the chamber wall remain in a non-contacting relationship.

170. The method of claim 169, wherein the member includes a tension member.

171. The method of claim 170, wherein the fixing step includes attaching a first anchor to a first end of the tension member and attaching a second anchor to a second end of the tension member.

172. The method of claim 171, wherein the fixing step includes engaging walls of the chamber external to the chamber with the first and second anchors.

173. The method of claim 169, wherein the placing step includes placing the member transverse the chamber.

174. The method of claim 169, wherein the placing step includes placing the member so that the member draws scar tissue of a chamber wall towards an opposite portion of the chamber wall.

175. A method for treating a heart, the method comprising the steps of:

placing a member within a heart chamber at portions of a wall of the chamber so that the member reduces a cross-sectional area of the chamber; and fixing the member to the chamber so that the portions of the chamber wall remain in a non-contacting relationship.

176. The method of claim 175, wherein the member includes a tension member.

177. The method of claim 176, wherein the fixing step includes attaching a first anchor to a first end of the tension member and attaching a second anchor to a second end of the tension member.

178. The method of claim 177, wherein the fixing step includes engaging walls of the chamber external to the chamber with the first and second anchors.

179. The method of claim 175, wherein the placing step includes placing the member transverse the chamber.

180. The method of claim 175, wherein the placing step includes placing the member so that the member draws scar tissue of a chamber wall towards an opposite portion of the chamber wall.

181. A method for treating a heart, the method comprising the steps of:

applying a force at a point on a wall of a heart chamber to change a shape of the chamber; and controlling the force such that a space remains between the wall proximate the point on the wall and an opposing wall of the chamber, wherein the force is applied and controlled by a member within the chamber and coupled to the point on the wall.

182. The method of claim 181, wherein the member includes anchors external the chamber.

183. The method of claim 181, wherein the member includes a tension member transverse the chamber.

* * * * *

UNITED STATES PATENT AND TRADEMARK OFFICE
CERTIFICATE OF CORRECTION

PATENT NO.    : 6,059,715
DATED         : May 9, 2000
INVENTOR(S)   : Cyril J. Schweich, Jr. and Todd J. Mortier It is certified that error appears in the above-identified patent and that said Letters Patent is hereby corrected as shown below:

<u>Column 6,</u>
Line 41, before "member", insert -- passive --.

<u>Column 7,</u>
Lines 7 and 38, before "member", insert -- passive --.
Line 11, after "remain in", insert -- a non-contacting relationship and --.

<u>Column 8,</u>
Lines 11 and 50, before "member", insert -- passive --.

<u>Column 9,</u>
Lines 7 and 9, "claim 59" should read -- claim 53 --.
Lines 25 and 65, before "member", insert -- passive --.

<u>Column 10,</u>
Line 39, before "member", insert -- passive --.

<u>Column 11,</u>
Line 18, before "controlling", insert -- passively --.
Line 45, before "member", insert -- passive --; and after "remain", insert -- completely --.
Line 47, after "chamber", delete "during systole".

<u>Column 12,</u>
Lines 13 and 29, before "member", insert -- passive --.
Line 36, after "member", insert -- , wherein the passive member is adapted to remain completely external to the chamber --.

UNITED STATES PATENT AND TRADEMARK OFFICE
CERTIFICATE OF CORRECTION

| | |
|---|---|
| PATENT NO. | : 6,059,715 |
| DATED | : May 9, 2000 |
| INVENTOR(S) | : Cyril J. Schweich, Jr. and Todd J. Mortier |

It is certified that error appears in the above-identified patent and that said Letters Patent is hereby corrected as shown below:

<u>Column 14,</u>
Line 2, "firstt" should read -- first --.
Line 17, "So" should read -- so --.

Signed and Sealed this

Nineteenth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,059,715
DATED : May 9, 2000
INVENTOR(S) : Cyril J. Schweich, Jr. and Todd J. Mortier It is certified that error appears in the above-identified patent and that said Letters Patent is hereby corrected as shown below:

<u>Column 6,</u>
Line 41, before "member", insert -- passive --.

<u>Column 7,</u>
Lines 7 and 38, before "member", insert -- passive --.
Line 11, after "remain in", insert -- a non-contacting relationship and --.

<u>Column 8,</u>
Lines 11 and 50, before "member", insert -- passive --.

<u>Column 9,</u>
Lines 7 and 9, "claim 59" should read -- claim 53 --.
Lines 25 and 65, before "member", insert -- passive --.

<u>Column 10,</u>
Line 39, before "member", insert -- passive --.

<u>Column 11,</u>
Line 18, before "controlling", insert -- passively --.
Line 45, before "member", insert -- passive --; and after "remain", insert -- completely --.
Line 47, after "chamber", delete "during systole".
Line 52, after "chamber" insert -- during systole --.

<u>Column 12,</u>
Lines 13 and 29, before "member", insert -- passive --.
Line 36, after "member", insert -- , wherein the passive member is adapted to remain completely external to the chamber --.

UNITED STATES PATENT AND TRADEMARK OFFICE
CERTIFICATE OF CORRECTION

PATENT NO.    : 6,059,715
DATED         : May 9, 2000
INVENTOR(S)   : Cyril J. Schweich, Jr. and Todd J. Mortier It is certified that error appears in the above-identified patent and that said Letters Patent is hereby corrected as shown below:

Column 14,
Line 2, "firstt" should read -- first --.
Line 17, "So" should read -- so --.

This certificate supersedes Certificate of Correction issued November 19, 2002.

Signed and Sealed this

Nineteenth Day of August, 2003

JAMES E. ROGAN
*Director of the United States Patent and Trademark Office*